United States Patent
Weingarten et al.

(10) Patent No.: US 12,257,082 B2
(45) Date of Patent: Mar. 25, 2025

(54) CONE BEAM COMPUTED TOMOGRAPHY INTEGRATION FOR CREATING A NAVIGATION PATHWAY TO A TARGET IN THE LUNG AND METHOD OF NAVIGATING TO THE TARGET

(71) Applicant: Covidien LP, Mansfield, MA (US)

(72) Inventors: Oren P. Weingarten, Hod-Hasharon (IL); Ariel Birenbaum, Raanana (IL); Evgeni Kopel, Barkan (IL)

(73) Assignee: Covidien LP, Mansfield, MA (US)

( * ) Notice: Subject to any disclaimer, the term of this patent is extended or adjusted under 35 U.S.C. 154(b) by 455 days.

(21) Appl. No.: 17/855,104

(22) Filed: Jun. 30, 2022

(65) Prior Publication Data

US 2024/0000399 A1    Jan. 4, 2024

(51) Int. Cl.
| | | |
|---|---|---|
| *A61B 10/04* | (2006.01) | |
| *A61B 5/05* | (2021.01) | |
| *A61B 6/00* | (2006.01) | |
| *A61B 6/03* | (2006.01) | |
| *A61B 6/40* | (2024.01) | |
| *A61B 90/11* | (2016.01) | |

(52) U.S. Cl.
CPC .............. *A61B 6/03* (2013.01); *A61B 6/4085* (2013.01); *A61B 6/4405* (2013.01); *A61B 6/5223* (2013.01); *A61B 90/11* (2016.02)

(58) Field of Classification Search
CPC ... A61B 1/00; A61B 1/00002; A61B 1/00009; A61B 1/0059; A61B 1/005; A61B 1/01; A61B 1/0125; A61B 1/041; A61B 1/042; A61B 34/10; A61B 34/20
See application file for complete search history.

(56) References Cited

U.S. PATENT DOCUMENTS

| | | |
|---|---|---|
| 8,335,359 B2 | 12/2012 | Fidrich et al. |
| 8,706,184 B2 | 4/2014 | Mohr et al. |
| 8,827,934 B2 | 9/2014 | Chopra et al. |
| 9,918,659 B2 | 3/2018 | Chopra et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |

(Continued)

FOREIGN PATENT DOCUMENTS

| | | |
|---|---|---|
| BR | 0013237 A | 7/2003 |
| BR | 0116004 A | 6/2004 |

(Continued)

*Primary Examiner* — Don K Wong
(74) *Attorney, Agent, or Firm* — Weber Rosselli & Cannon LLP

(57) ABSTRACT

A method of performing a surgical procedure includes obtaining images of a patient's anatomy using a cone beam computed tomography machine while the patient is sedated, identifying an area of interest in the images obtained by the cone beam computed tomography machine, identifying a pathway to the identified area of interest using the images obtained by the cone beam computed tomography machine, and navigating a catheter within the patient's airways to the identified area of interest using the identified pathway.

20 Claims, 11 Drawing Sheets

(56) References Cited

U.S. PATENT DOCUMENTS

| | | |
|---|---|---|
| 10,555,788 B2 | 2/2020 | Panescu et al. |
| 10,610,306 B2 | 4/2020 | Chopra |
| 10,638,953 B2 | 5/2020 | Duindam et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 2003/0013972 A1 | 1/2003 | Makin |
| 2013/0225943 A1* | 8/2013 | Holsing ............... A61B 6/12 600/409 |
| 2013/0303945 A1 | 11/2013 | Blumenkranz et al. |
| 2014/0035798 A1 | 2/2014 | Kawada et al. |
| 2015/0148690 A1 | 5/2015 | Chopra et al. |
| 2015/0265368 A1 | 9/2015 | Chopra et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0112576 A1 | 4/2017 | Coste-Maniere et al. |
| 2017/0209071 A1 | 7/2017 | Zhao et al. |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0155116 A1 | 5/2020 | Donhowe et al. |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |

FOREIGN PATENT DOCUMENTS

| | | |
|---|---|---|
| CZ | 486540 B1 | 9/2016 |
| CZ | 2709512 B6 | 8/2017 |
| CZ | 2884879 B1 | 1/2020 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | PA03005028 A | 1/2004 |
| MX | 225663 B | 1/2005 |
| MX | 226292 B | 2/2005 |
| MX | 246862 B | 6/2007 |
| MX | 265247 B | 3/2009 |
| MX | 284569 B | 3/2011 |

* cited by examiner

CONE BEAM COMPUTED TOMOGRAPHY INTEGRATION FOR CREATING A NAVIGATION PATHWAY TO A TARGET IN THE LUNG AND METHOD OF NAVIGATING TO THE TARGET

BACKGROUND

Technical Field

The present disclosure relates to the field of navigation of medical devices within a patient, and in particular, planning a pathway through a luminal network of a patient and navigating medical devices to a target.

Description of Related Art

There are several commonly applied medical methods, such as endoscopic procedures or minimally invasive procedures, for treating various maladies affecting organs including the liver, brain, heart, lungs, gall bladder, kidneys, and bones. Often, one or more imaging modalities, such as magnetic resonance imaging (MM), ultrasound imaging, computed tomography (CT), cone-beam computed tomography (CBCT) or fluoroscopy (including 3D fluoroscopy) are employed by clinicians to identify and navigate to areas of interest within a patient and ultimately a target for biopsy or treatment. In some procedures, pre-operative scans may be utilized for target identification and intraoperative guidance. However, real-time imaging may be required to obtain a more accurate and current image of the target area. Furthermore, real-time image data displaying the current location of a medical device with respect to the target and its surroundings may be needed to navigate the medical device to the target in a safe and accurate manner (e.g., without causing damage to other organs or tissue).

For example, an endoscopic approach has proven useful in navigating to areas of interest within a patient. To enable the endoscopic approach endoscopic navigation systems have been developed that use previously acquired Mill data or CT image data to generate a three-dimensional (3D) rendering, model, or volume of the particular body part such as the lungs.

In some applications, the acquired Mill data or CT Image data may be acquired during the procedure (perioperatively). The resulting volume generated from the Mill scan or CT scan is then utilized to create a navigation plan to facilitate the advancement of the endoscope (or other suitable medical device) within the patient anatomy to an area of interest. In some cases, the volume generated may be used to update a previously created navigation plan. A locating or tracking system, such as an electromagnetic (EM) tracking system, or fiber-optic shape sensing system may be utilized in conjunction with, for example, CT data, to facilitate guidance of the endoscope to the area of interest.

However, CT-to-body divergence can cause inaccuracies in navigation using locating or tracking systems, leading to the use of fluoroscopic navigation to identify a current position of the medical device and correcting the location of the medical device in the 3D model. As can be appreciated, these inaccuracies can lead to increased surgical times to correct the real-time position of the medical device within the 3D models and the use of fluoroscopy leads to additional set-up time and radiation exposure.

SUMMARY

In accordance with the present disclosure, a method of performing a surgical procedure includes obtaining images of a patient's anatomy using a cone beam computed tomography machine while the patient is sedated, identifying an area of interest in the images obtained by the cone beam computed tomography machine, identifying a pathway to the identified area of interest using the images obtained by the cone beam computed tomography machine, and navigating a catheter within the patient's airways to the identified area of interest.

In aspects, obtaining the images of the patient's anatomy may include obtaining the images of a patient's anatomy using a fixed cone beam computed tomography machine while the patient is sedated.

In other aspects, obtaining the images of the patient's anatomy may include obtaining the images of a patient's anatomy using a mobile cone beam computed tomography machine while the patient is sedated.

In certain aspects, the method may include generating a three-dimensional model of the patient's anatomy from the images obtained by the cone beam computed tomography machine.

In aspects, identifying the area of interest may include identifying the area of interest within the three-dimensional model of the patient's anatomy.

In certain aspects, the method may include registering a location of the catheter within the patient's anatomy to the images obtained by the cone beam computed tomography machine.

In other aspects, obtaining images of the patient's anatomy may include obtaining images of the patient's anatomy using the cone beam computed tomography machine while the patient is sedated and before advancement of the catheter within the patient's body cavity.

In accordance with another aspect of the present disclosure, a method of performing a surgical procedure includes navigating a catheter to a lobe of a patient's lung including an area of interest, obtaining images of the patient's anatomy using a cone beam computed tomography machine, identifying the area of interest in the images obtained by the cone beam computed tomography machine, identifying a pathway to the area of interest using the images obtained by the cone beam computed tomography machine, and navigating the catheter to the area of interest using the identified pathway.

In aspects, obtaining the images of the patient's anatomy may include obtaining the images of a patient's anatomy using a fixed cone beam computed tomography machine.

In other aspects, obtaining the images of the patient's anatomy may include obtaining the images of a patient's anatomy using a mobile cone beam computed tomography machine.

In certain aspects, the method may include generating a three-dimensional model of the patient's anatomy from the images obtained by the cone beam computed tomography machine.

In other aspects, identifying the area of interest may include identifying the area of interest within the three-dimensional model of the patient's anatomy.

In aspects, the method may include registering a location of the catheter within the patient's anatomy to the images obtained by the cone beam computed tomography machine.

In certain aspects, the method may include obtaining an anteroposterior image of the patient's anatomy using the cone beam computed tomography machine and identifying an angle of the cone beam computed tomography machine when the anteroposterior image was obtained.

In other aspects, the method may include identifying a location of a portion of the catheter within the images obtained by the cone beam computed tomography machine.

In aspects, the method may include registering the identified location of the catheter to the images obtained by the cone beam computed tomography machine.

In accordance with another aspect of the present disclosure, a system for performing a surgical procedure includes a cone beam computed tomography machine, a catheter configured to be navigated within a patient's airways, and a controller operably coupled to the cone beam computed tomography machine, the controller including a memory and a processor, the memory storing instructions, which when executed by the processor cause the processor to obtain images of a patient's anatomy using the cone beam computed tomography machine while the patient is sedated, identify an area of interest in the images obtained by the cone beam computed tomography machine, identify a pathway to the identified area of interest using the images obtained by the cone beam computed tomography machine, and aid navigation of the catheter within the patient's airways to the identified area of interest using the identified pathway.

In aspects, the cone beam computed tomography machine is a fixed cone beam computed tomography machine.

In other aspects, the cone beam computed tomography machine is a mobile cone beam computed tomography machine.

In certain aspects, the instructions, when executed by the processor, may cause the processor to obtain images of the patient's anatomy using the cone beam computed tomography machine while the patient is sedated and before advancement of the catheter within the patient's body cavity.

BRIEF DESCRIPTION OF THE DRAWINGS

Various aspects and embodiments of the disclosure are described hereinbelow with references to the drawings, wherein.

DETAILED DESCRIPTION

The present disclosure is directed to surgical imaging system, and more particularly, to system and methods for assisting a clinician in navigation of endoscopes, catheters, and tools to area of interest or targets within a patient for biopsy and therapy while reducing the number of times a patient must be imaged and increasing the accuracy of the navigational model. The system and methods include utilizing fixed or mobile cone beam computed tomography (CBCT) machines to obtain intra-procedural images of the patient's anatomy. The intra-procedural images can be used in lieu of pre-procedural images or otherwise update models, pathways, and/or plans generated using pre-procedural images. It is envisioned that inputs may be made on a user interface to identify a position of the endoscope and/or area of interest within the intra-procedural images to increase the accuracy of a registration between the position of the endoscope and/or area of interest within the model generated from the intra-procedural images. Although generally described with reference to the lung, it is contemplated that the systems and methods described herein may be used with any structure within the patient's body, such as the liver, kidney, prostate, gynecological, amongst others.

Figure 1:
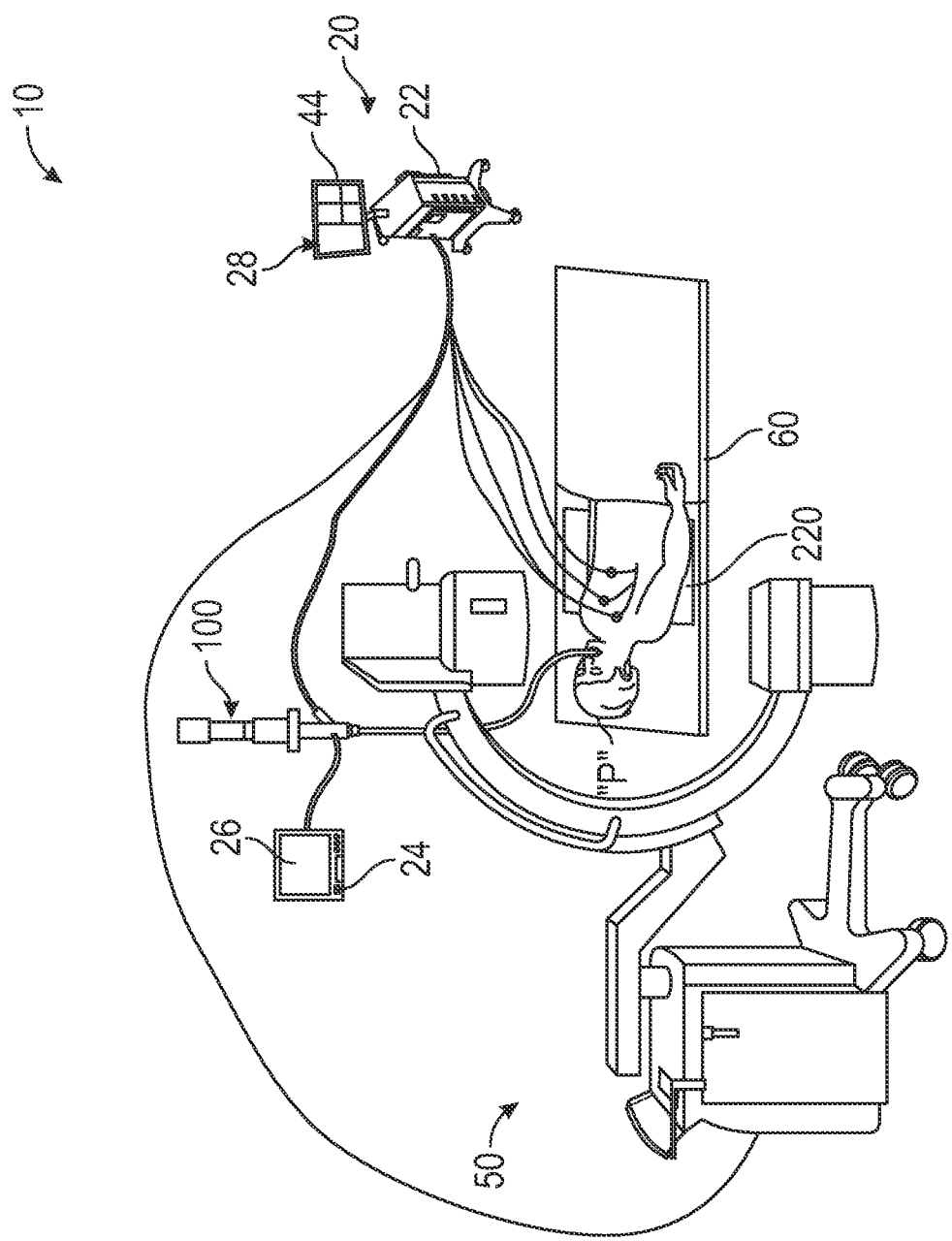
FIG. 1 is a schematic view of a surgical system provided in accordance with the present disclosure.

Turning now to the drawings, FIG. 1 illustrates a surgical system for navigating a surgical instrument to an area of interest in accordance with the present disclosure and generally identified by reference numeral 10. The surgical system 10 includes an endoscope or catheter 100, a workstation 20 operably coupled to the endoscope or catheter 100, and a Cone Beam Computed Tomography (CBCT) machine 50 operably coupled to the workstation 20. The patient is shown lying on an operating table 60 with the endoscope or catheter 100 inserted through the patient's mouth and into the patient's airways, although it is contemplated that the endoscope or catheter 100 may be inserted into any suitable body cavity of the patient, depending upon the procedure being performed.

Figure 2:
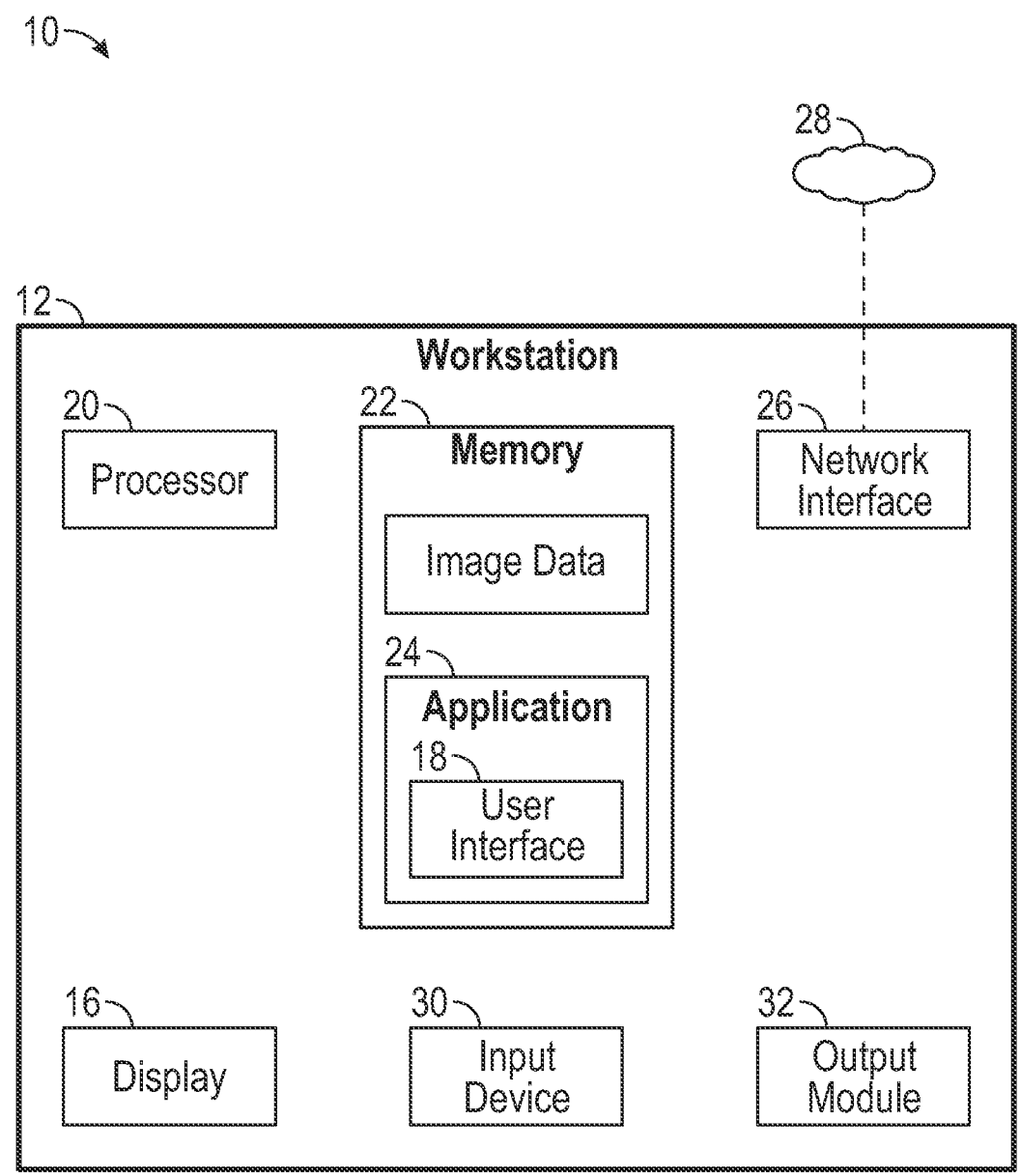
FIG. 2 is a schematic view of a controller of the surgical system of FIG. 1.

Continuing with FIG. 1 and with additional reference to FIG. 2, the workstation 20 includes a computer 22 and a display 24 that is configured to display one or more user interfaces 26 and 28. The workstation 20 may be a desktop computer or a tower configuration with the display 24 or may be a laptop computer or other computing device. The workstation 20 includes a processor 30 which executes software stored in a memory 32. The memory 32 may store video or other imaging data captured by the endoscope or catheter 100 or pre-procedure images from, for example, a computer-tomography (CT) scan, Positron emission tomography (PET), Magnetic Resonance Imaging (MRI), Cone-Beam CT, amongst others. In addition, the memory 32 may store one or more applications 34 to be executed on the processor 30. Through not explicitly illustrated, the display 24 may be incorporated into a head mounted display such as an augmented reality (AR) headset such as the HoloLens offered by Microsoft Corp.

A network interface 36 enables the workstation 20 to communicate with a variety of other devices and systems via the Internet. The network interface 36 may connect the workstation to the Internet via a wired or wireless connection. Additionally, or alternatively, the communication may be via an ad-hoc Bluetooth® or wireless networks enabling communication with a wide-area network (WAN) and/or a local area network (LAN). The network interface 36 may connect to the Internet via one or more gateways, routers, and network address translation (NAT) devices. The network interface 36 may communicate with a cloud storage system 38, in which further image data and videos may be stored. The cloud storage system 38 may be remote from or on the premises of the hospital such as in a control or hospital information technology room. An input device 40 receives inputs from an input device such as a keyboard, a mouse, voice commands, amongst others. An output module 42 connects the processor 30 and the memory 32 to a variety of output devices such as the display 24. It is envisioned that the output module 42 may include any connectivity port or bus, such as, for example, parallel ports, serial ports, universal serial busses (USB), or any other similar connectivity port known to those skilled in the art. In embodiments, the workstation 20 may include its own display 44, which may be touchscreen display.

In embodiments, the network interface 36 may couple the workstation 20 to a Hospital Information System (HIS) to enable the review of patient information. As such, the workstation includes a synthesizer which communicates with the HIS either directly or through a cloud computing network via a hardwired connection or wirelessly. Information accessible by the system includes information stored on a Picture Archiving and Communication system (PACS), a Radiology Information System (RIS), an Electronic Medical Records System (EMR), a Laboratory Information System (LIS), and in embodiments, a Cost and Inventory System (CIS), wherein each of which communicates with the HIS. Although generally described as utilizing the HIS, it is envisioned that the patient information may be obtained from any other suitable source, such as private office, compact-disc (CD) or other storage medium, etc.

The system 10 includes a Patient/Surgeon Interface System or Synthesizer which enables communication with the HIS and its associated database. Using information gathered from the HIS, an Area of Interest (AOI) is able to be identified illustrating the effects of lung disease, and in embodiments, the software application associated with the synthesizer may be able to automatically identify areas of interest and present these identified areas to a clinician for review via the user interface 26. In embodiments, pre-procedure image data gathered from the HIS is processed by the software application to generate a three-dimensional (3D) reconstruction of the patient's lungs, and using medical information gathered from the HIS, such as, for example, prior surgical procedures, diagnosis of common lung conditions such as Chronic Pulmonary Obstruction Disorder (COPD), and the location of common structures within the patient's body cavity, the software application generates a 3D model of the patient's lungs incorporating this information. In embodiments, the system 10 may facilitate an approach of a medical device to the target area using Electromagnetic Navigation (EMN) and for determining the location of a medical device with respect to the AOI. One such EMN system is the ILLUMISITE system currently sold by Medtronic PLC, though other systems for intraluminal navigation are considered within the scope of the disclosure including shape sensing technology which detect the shape of the distal portion of the catheter and match that shape to the shape of the luminal network in a 3D model.

In embodiments, the CBCT machine 50 may be a fixed CBCT machine or a mobile CBCT machine. In one embodiment, the fixed CBCT machine 50 is utilized to scan the patient during the surgical procedure but before the endoscope or catheter 100 is inserted within the patient's airways. In this manner, the patient is sedated or otherwise under anesthesia to ensure that the patient is generally immobilized during the scan performed by the fixed CBCT machine Once the scan has been completed, the images captured by the fixed CBCT machine 50 are saved on a memory associated with fixed CBCT machine 50. It is envisioned that the images captured by the fixed CBCT machine 50 and saved on the memory may be transferred to the workstation 20 via any suitable means, such as via the internet or intranet (e.g., PACS, etc.), via computer readable storage media (e.g., memory stick, CD-ROM, etc.), amongst others.

With the images captured by the fixed CBCT machine 50 received by the workstation 20, a planning phase for generating and viewing a 3D model of the patient's anatomy, enabling the identification of target tissue ("TT") on the 3D model (automatically, semi-automatically, or manually), and in embodiments, allowing for the selection of a pathway ("PW") through the patient's anatomy to the target tissue. One example of such an application is the ILLUMISITE® planning and navigation suites currently marketed by Medtronic. The 3D model may be displayed on the display 24 or another suitable display (not shown) associated with the controller 20, or in any other suitable fashion. Using the controller 20, various views of the 3D model may be provided and/or the 3D model may be manipulated to facilitate identification of target tissue on the 3D model and/or selection of a suitable pathway to the target tissue. With the pathway to the target tissue selected, the endoscope or catheter 100 is inserted within the patient's airways and the detected location and/or images obtained by the endoscope or catheter 100 within the patient's airways is automatically registered to the 3D model.

In embodiments, the 3D model generated from the images acquired by the fixed CBCT machine 50 can be utilized to update or otherwise correct a 3D model generated from the pre-procedure images. In this manner, the navigation of the endoscope or catheter 100 to the target tissue is completed using up to date information regarding the condition of the patient's lungs and reduces the need to perform additional intra-operative imaging to verify the location of the endoscope or catheter 100 within patient's airways during navigation to the target tissue and/or before treatment of the target tissue. It is envisioned that the 3D model or images obtained by the fixed CBCT machine 50 may be overlaid or otherwise associated with an intra-operative image (e.g., fixed CBCT machine 50 images, images captured by the endoscope or catheter 100, fluoroscopic images, etc.).

In another embodiment, before the surgical procedure begins, the software application utilizes pre-procedure image data stored on the memory 32 or via the HIS and is processed by the software application to generate a three-dimensional (3D) reconstruction of the patient's lungs, identify target tissue on the 3D model (automatically, semi-automatically, or manually), and in embodiments, allowing for the selection of a pathway ("PW") through the patient's anatomy to the target tissue. With the pathway to the target tissue selected, the endoscope or catheter 100 is inserted within the patient's airways and the detected location of the endoscope or catheter 100 within the patient's airways is automatically registered to the 3D model. The endoscope or catheter 100 is then navigated to a portion of the lobe of the patient's lung in which the target tissue is located. Although generally described as utilizing a 3D model to aid navigation of the endoscope or catheter 100 to the lobe in which the target tissue is located, it is envisioned that the endoscope or catheter 100 may be manually navigated to the lobe in which the target tissue is located without the aid of a navigation tool.

Once the endoscope is located within the lobe in which the target tissue is located, intra-procedure images are obtained from a mobile CBCT machine 50 and transferred to the workstation 20. The application generates a 3D model of the patient's anatomy using the intra-procedure images obtained from the mobile CBCT machine 50. The software application enables a user to enter the planning phase to identify of target tissue ("TT") on the 3D model (automatically, semi-automatically, or manually), and in embodiments, may allow for the selection of a pathway ("PW") through the patient's anatomy to the target tissue. With the pathway to the target tissue selected, the 3D model generated from the images obtained by the mobile CBCT machine 50 is registered (either manually or automatically) to the real time images obtained by the endoscope or catheter 100, or in embodiments, updates or otherwise replaces the 3D model generated from the pre-procedure image data and navigation to the target tissue is completed using the updated 3D model.

In embodiments, the software application permits the user to select and/or mark the location of the endoscope within the 3D model generated from the imaged obtained by the intra-operative mobile CBCT machine 50 to updated and/or correct differences between the initial 3D model generated from the pre-procedure images and the intra-operative images obtained by the mobile CBCT machine 50.

Figure 3:
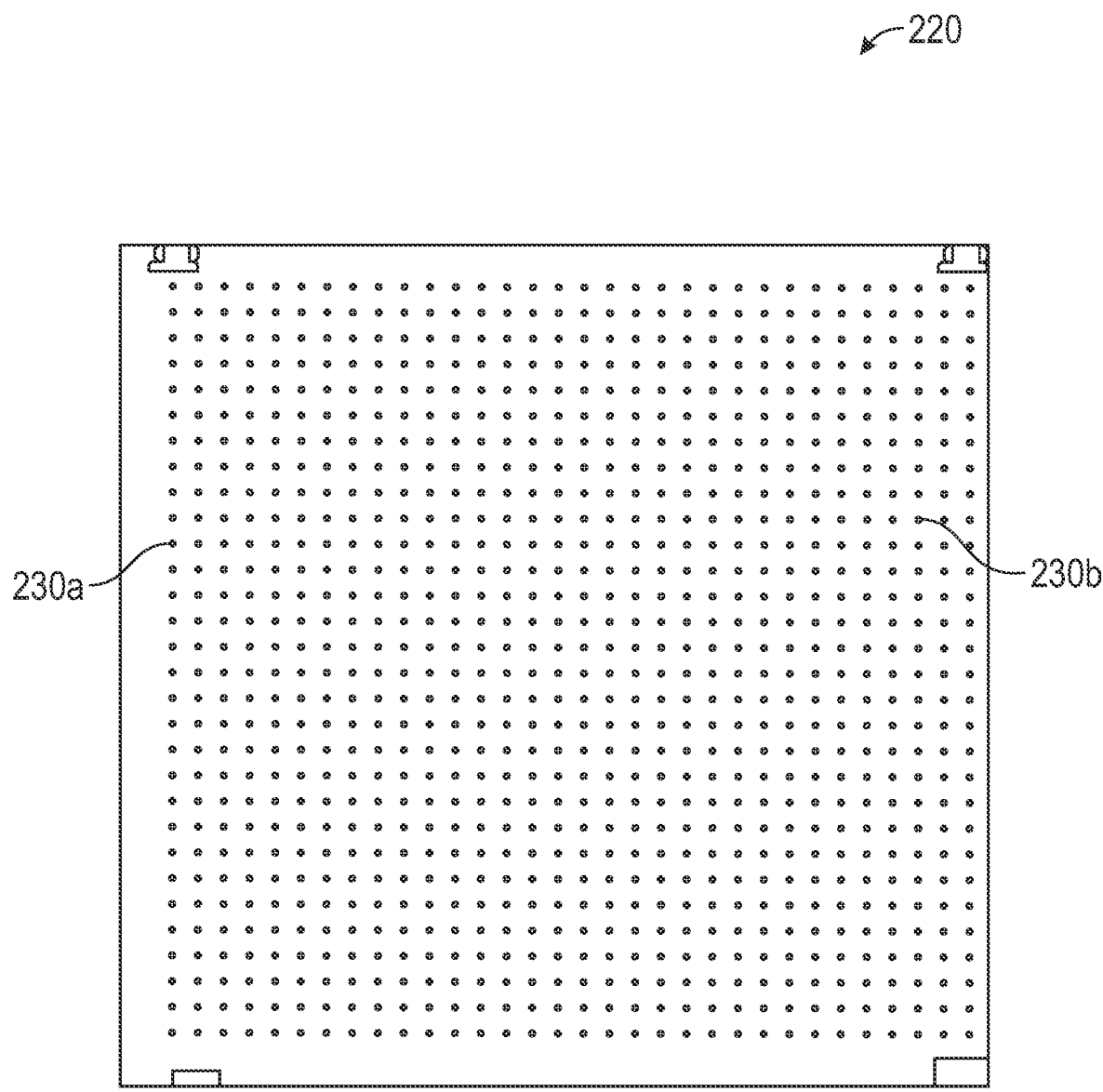
FIG. 3 is a schematic illustration of a two-dimensional grid structure of markers in accordance with the present disclosure.
Figure 4:
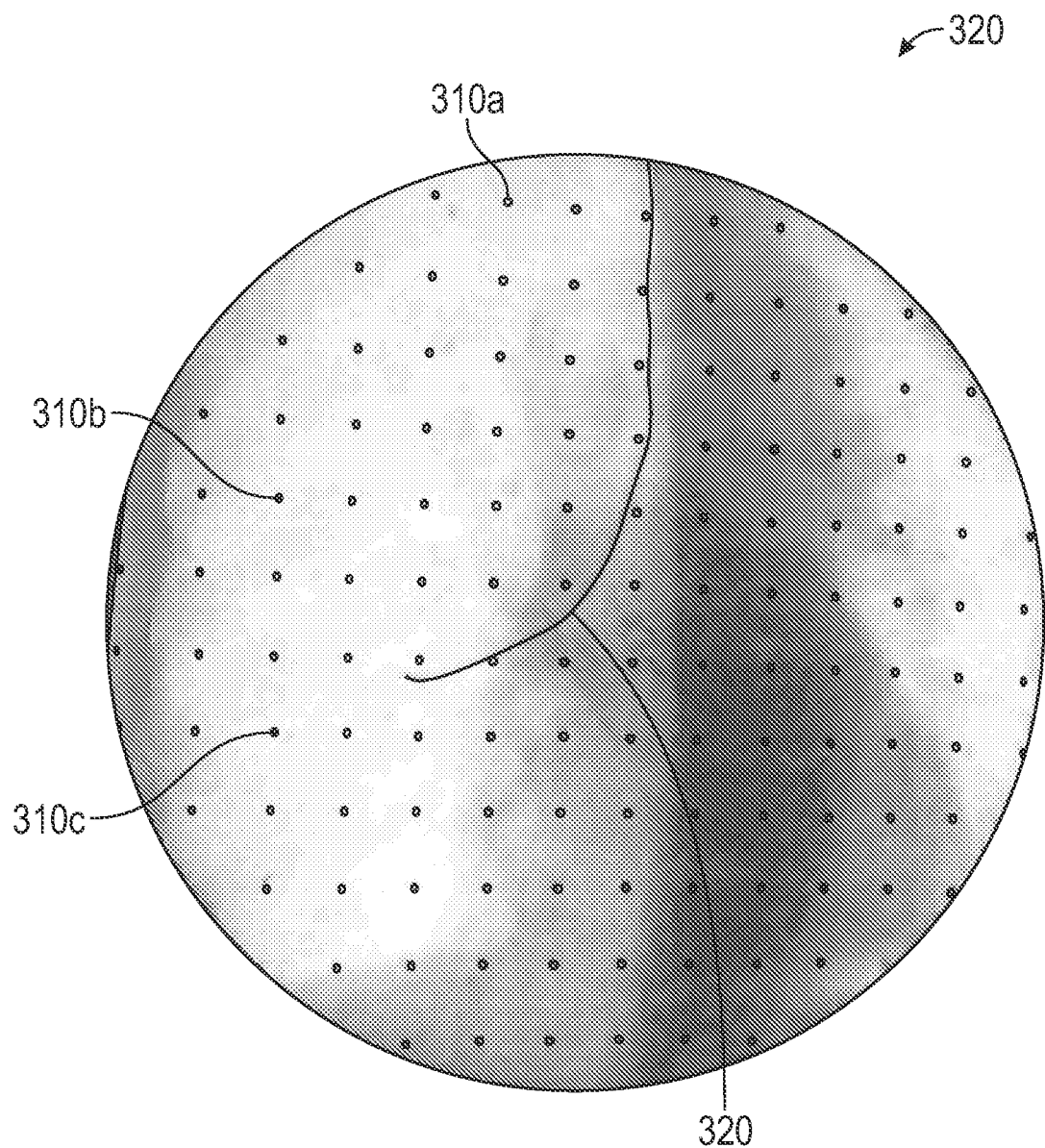
FIG. 4 is an exemplary image of a surgical site including the two-dimensional grid structure of FIG. 3 illustrated captured therein.

With additional reference to FIGS. 3 and 4, in an embodiment, the patient is laying on a two-dimensional (2D) grid structure of sphere markers 220 including sphere-shaped markers, such as sphere markers 230a and 230b, arranged in a two-dimensional grid pattern. The endoscope or catheter 100 is manually navigated within the patient's airways without the use of 3D navigation to the lobe of the patient's lungs in which the target tissue is located (the target lobe). Once the endoscope or catheter 100 is located within the target lobe, the mobile CBCT machine 50 is utilized to capture an image of the patient's lungs from an anteroposterior (AP) direction to identify an angle of the mobile CBCT machine 50 relative to the operating table 60. As can be appreciated, the CBCT machine 50 (either fixed or mobile) includes a narrower scan angle as compared to fluoroscopic imaging, and therefore, it is envisioned that the 2D grid structure may include fewer sphere markers 230a, 230b to decrease the number of artifacts present within the 3D model generated from the images obtained by the mobile CBCT machine 50. With the angle of the mobile CBCT machine 50 relative to the operating table 60 known, the mobile CBCT machine 50 is utilized to obtain a plurality of images of the patient's anatomy and generate a 3D model, as described hereinabove. The 3D model may be displayed to the user on the user interface 26 and the user is permitted to mark or otherwise indicate a position of the endoscope or catheter 100 within the images obtained by the mobile CBCT machine 50. Although generally described as being performed manually, it is envisioned that marking the location of the endoscope or catheter 100 within the intra-procedure images obtained by the mobile CBCT machine 50 may be automated by the software application.

With the location of the endoscope or catheter 100 identified within the intra-procedure images obtained by the mobile CBCT machine 50, the position of the endoscope or catheter 100 is registered to the 3D model (manually or automatically) and navigation to the target tissue is continued. In embodiments, one or more further scans by the mobile CBCT machine 50 to further update and/or confirm the position of the endoscope or catheter 100 within the patient's airways or relative to the target tissue.

In embodiments, rather than manually navigating the endoscope or catheter 100 to the target lobe, it is envisioned that the endoscope or catheter 100 may be navigated to the target lobe utilizing a 3D model formed from pre-procedure images obtained by the system 10, as described in further detail hereinabove. It is envisioned that the user may choose to manually navigate the endoscope or catheter 100 to the target lobe or may utilize a navigation aid utilizing the 3D model generated from pre-procedure images.

In some embodiments, during navigation of the endoscope or catheter 100 within the patient's airways using a 3D model constructed of pre-procedure images, the mobile CBCT machine 50 may be utilized to capture an intra-operative 2D video of the surgical site and generate a composite utilizing tomosynthesis. Utilizing a volume reconstructed from tomosynthesis of the 2D video, the location of the catheter within the images is identified (manually or automatically) and registration is completed. In embodiments, the 2D video captured by the mobile CBCT machine 50 may be captured during navigation of the endoscope or catheter 100 through the patient's airways using a 3D model generated using pre-procedure images. The 2D video is continuously displayed to the user during navigation to provide real-time corrections of the location of the endoscope or catheter 100 displayed on the 3D model. It is envisioned that the user may be able to provide inputs on the user interface 26 to identify a path through the patient's airways to reach the target tissue. In this manner, the software application utilizes the user inputs to create a pathway through the patient's airways corresponding to the user's inputs on the user interface 26.

Figure 5:
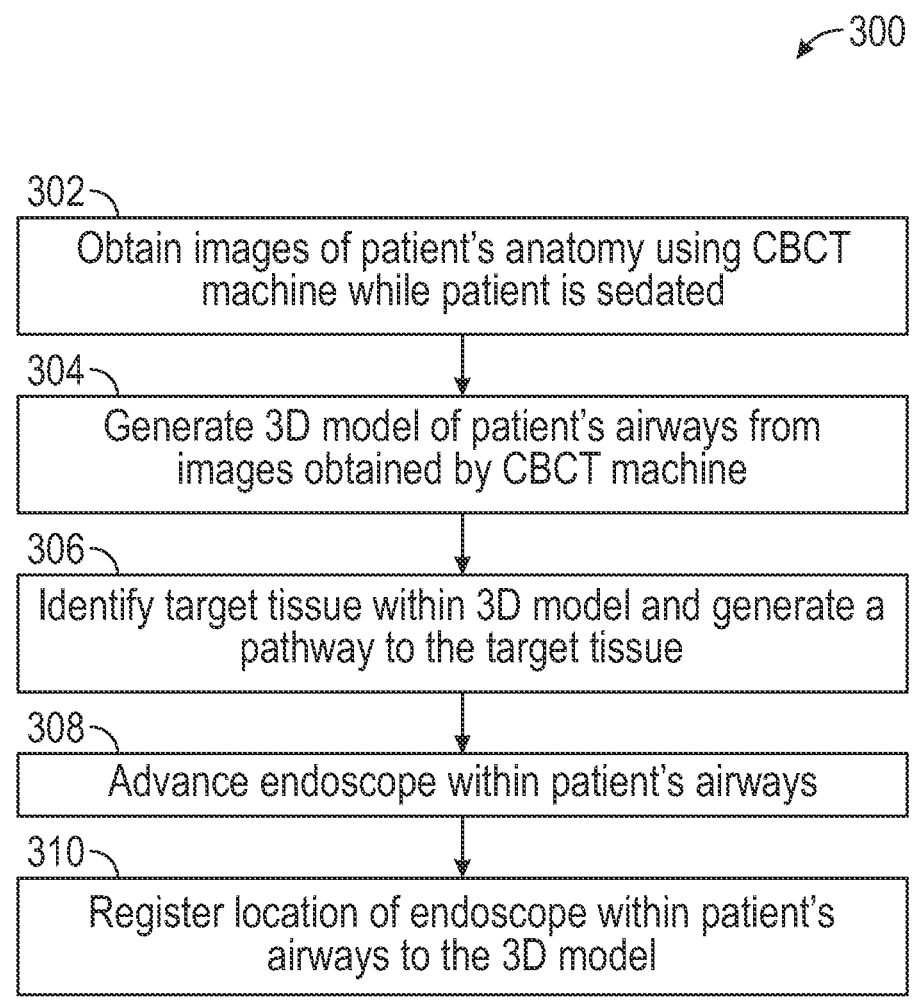
FIG. 5 is a flow diagram illustrating a method of performing a surgical procedure in accordance with aspects of the present disclosure.

Turning to FIG. 5, a method of navigating a surgical instrument to an area of interest is illustrated and generally identified by reference numeral 300. Initially, in step 302 images of the patient's lungs are obtained using the CBCT machine 50 while the patient is sedated or otherwise under anesthesia. In step 304, a 3D model of the patient's airways and/or lungs is generated using the images obtained by the CBCT machine 50. Using the generated 3D model, in step 306, target tissue is identified within the 3D model and a pathway to the target tissue is identified and displayed to the user on the user interface 26. With the 3D model generated and the pathway to the target tissue selected, the endoscope or catheter 100 is advanced within the patient's airways in step 308. In step 310, the location of the endoscope or catheter 100 is registered to the 3D model, and in step 312, the endoscope or catheter 100 is navigated to the area of interest.

Figure 6:
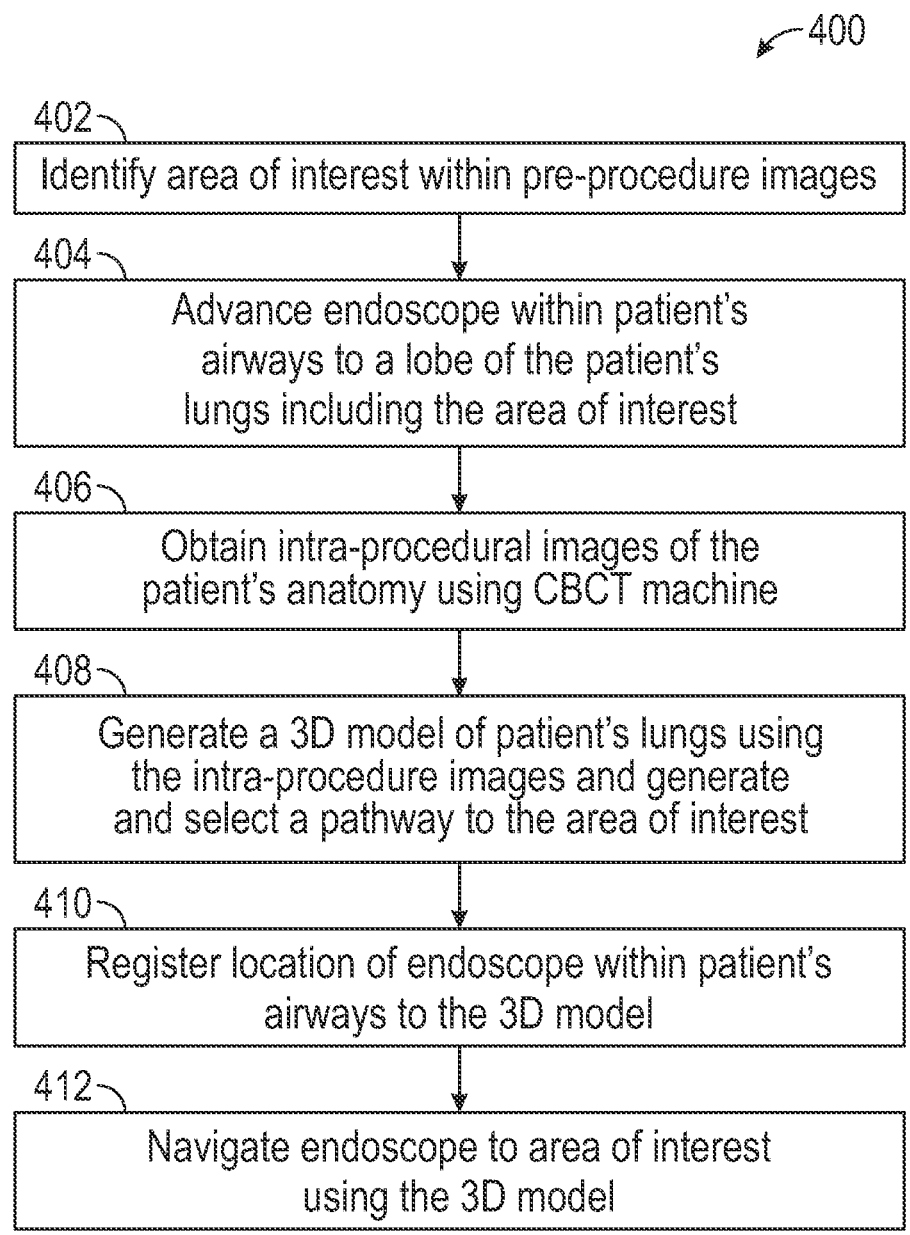
FIG. 6 is a flow diagram illustrating another method of performing a surgical procedure in accordance with aspects of the present disclosure.

With reference to FIG. 6, another embodiment of a method of navigating a surgical instrument to an area of interest is illustrated and generally identified by reference numeral 400. Initially, in step 402, an area of interest is identified within the patient's lungs using pre-procedure images. In step 404, the endoscope or catheter 100 is advanced within the patient's airways to a lobe of the patient's lungs in which the area of interest is located. Once located within the target lobe, the patient is imaged using the CBCT machine 50 in step 406. Using the images obtained by the CBCT machine 50, a 3D model of the patient's lungs is generated and a pathway to the identified area of interest is selected in step 408. At this point, in step 410, the position of the endoscope or catheter 100 within the target lobe is registered to the 3D model, and in step 412, the endoscope or catheter 100 is navigated to the area of interest.

Figure 7:
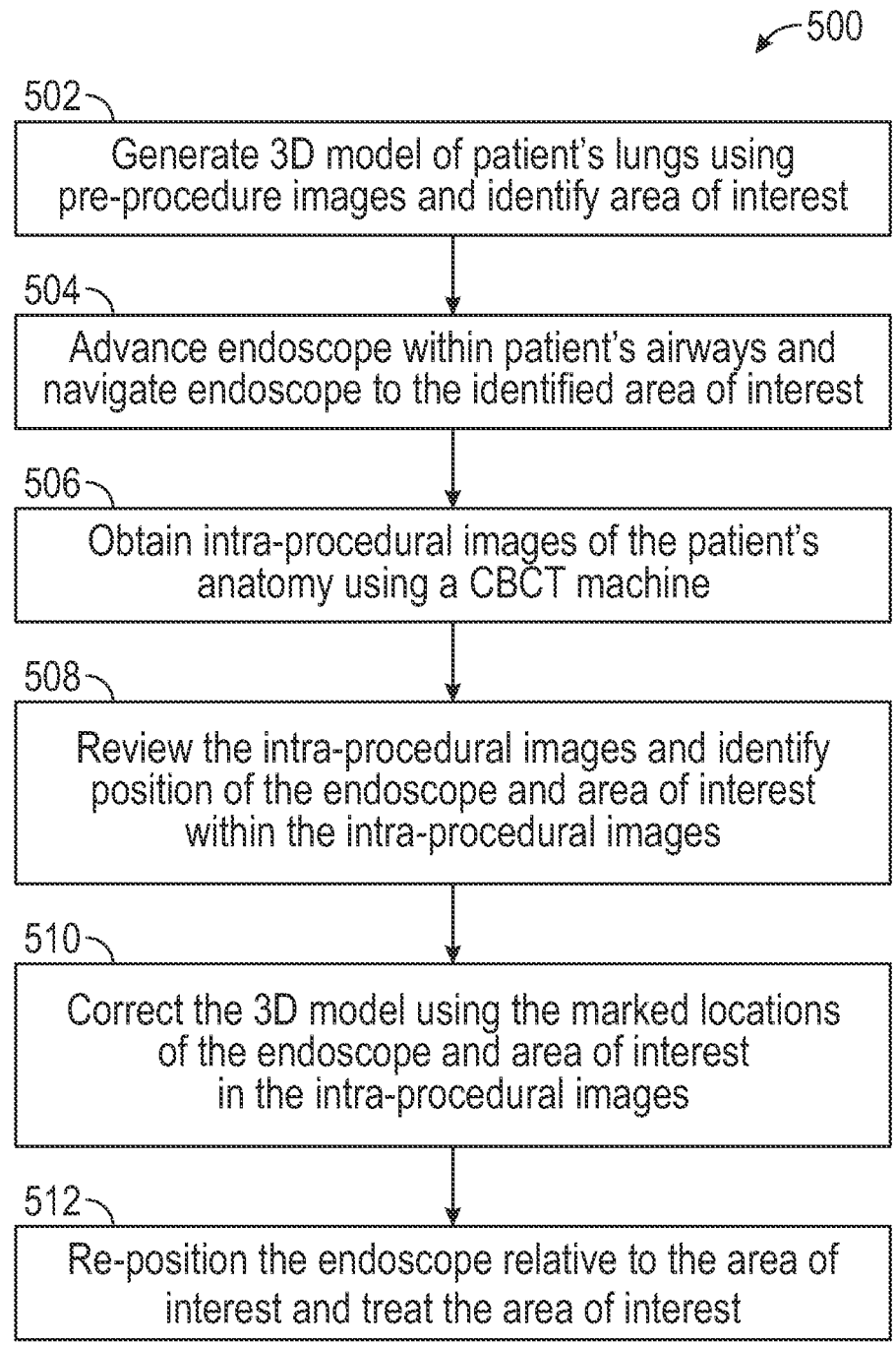
FIG. 7 is a flow diagram illustrating yet another method of performing a surgical procedure in accordance with aspects of the present disclosure.

Turning to FIG. 7, yet another embodiment of a method of navigating a surgical instrument to an area of interest is illustrated and generally identified by reference numeral 500. In step 502, a 3D model of the patient's lungs is generated from pre-procedure images and an area of interest is identified within the 3D model. In step 504, the endoscope or catheter 100 is advanced within the patient's airways and navigated to the identified area of interest. With the endoscope or catheter 100 located adjacent the area of interest, the patient's anatomy is imaged with the CBCT machine 50 in step 506. The images captured by the CBCT machine 50 are reviewed and in step 508, the location of the endoscope or catheter 100 and the area of interest is marked or otherwise identified in the user interface 26. In step 510, the system corrects the 3D model generated with pre-procedure images using the marked locations of the endoscope or catheter 100 and the area of interest and in step 512, the endoscope is re-positioned relative to the area of interest and the area of interest is treated.

Figure 8:
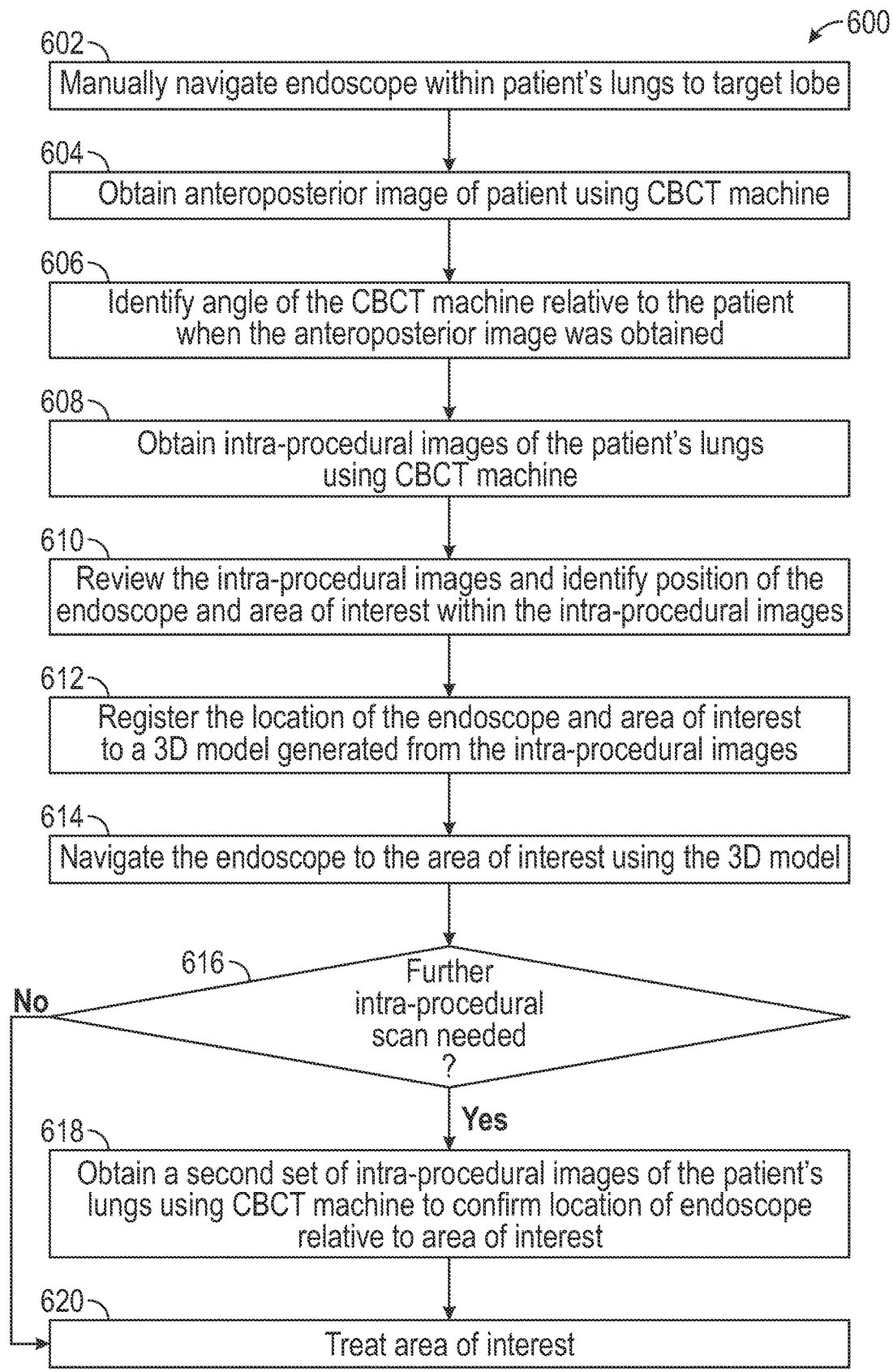
FIG. 8 is a flow diagram illustrating still another method of performing a surgical procedure in accordance with aspects of the present disclosure.

With reference to FIG. 8, still another embodiment of a method of navigating a surgical instrument to an area of interest is illustrated and generally identified by reference numeral 600. Initially, in step 602, the endoscope or catheter 100 is navigated to the target lobe manually and without assistance of guidance. In step 604, an anteroposterior image of the patient's lungs is obtained by the CBCT machine 50 and in step 606, the CBCT machine 50 is centered and an angle of the CBCT machine 50 relative to the bed 60 is identified using the (2D) grid structure of sphere markers 220. In step 608, the patient's lungs are imaged using the CBCT machine 50. The intra-procedure images captured by the CBCT machine 50 are reviewed and the position of the endoscope or catheter 100 and the area of interest within the intra-procedure images are marked or otherwise indicated in the user interface 26 in step 610. In step 612, the position of the endoscope or catheter 100 and the area of interest are registered to a 3D model generated from the intra-procedural images and in step 614, the endoscope or catheter 100 is navigated to the area of interest using the 3D model. In step 616, it is determined if a further intra-operative scan using the CBCT machine 50 is necessary, and if so, the patient's anatomy is imaged a second time using the CBCT machine 50 to confirm the location of the endoscope or catheter 100 relative to the area of interest in step 618. With the location of the endoscope or catheter 100 relative to the area of interest confirmed, the area of interest is treated in step 620. If no further scan is required, step 618 is skipped and the area of interest is treated in step 620.

Figure 9:
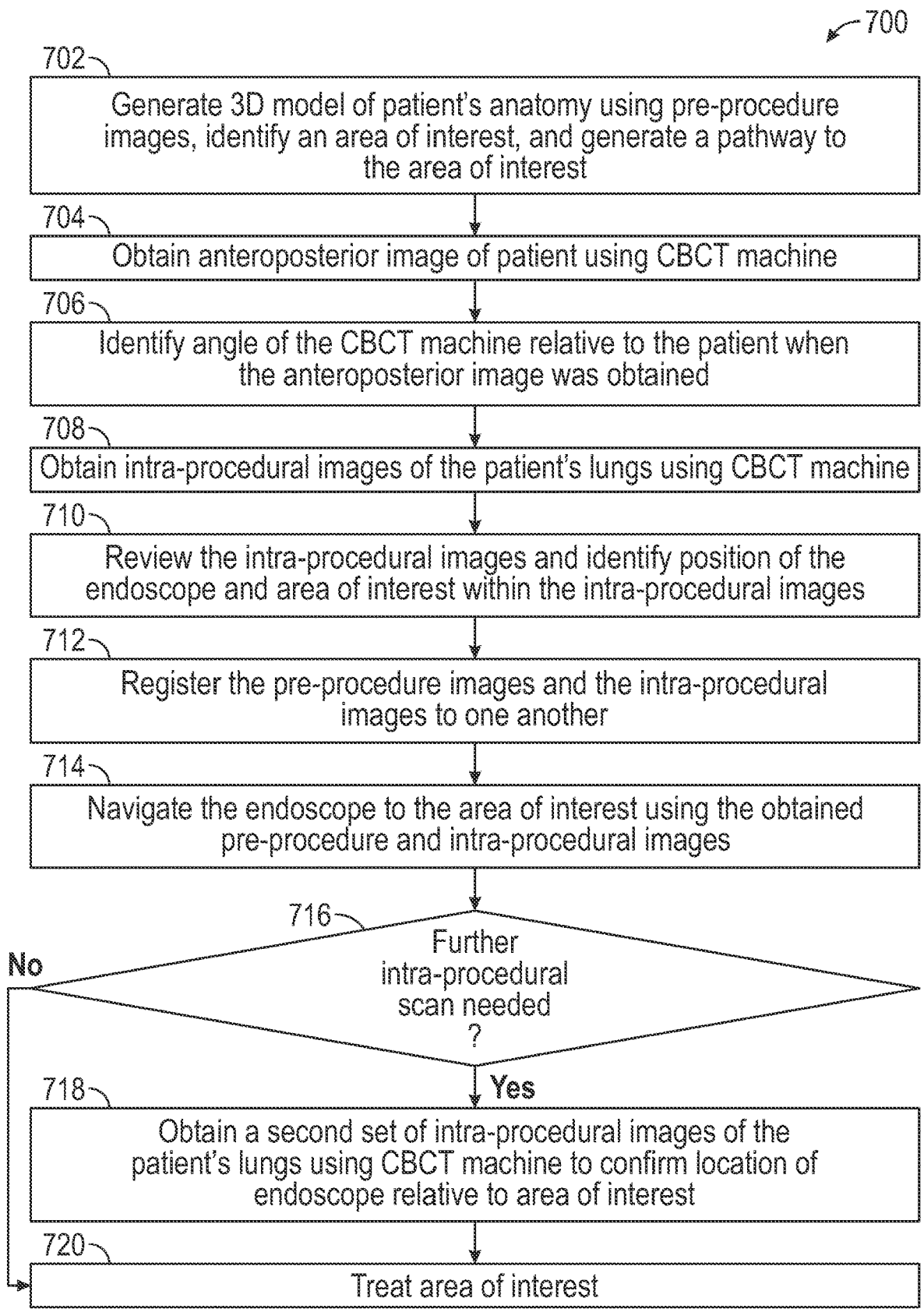
FIG. 9 is a flow diagram illustrating another method of performing a surgical procedure in accordance with aspects of the present disclosure.

Turning to FIG. 9, another embodiment of a method of navigating a surgical instrument to an area of interest is illustrated and generally identified by reference numeral 700. Initially, in step 702, a 3D model is generated from pre-procedure images and an area of interest, and a pathway thereto, is identified in the 3D model. In step 704, an anteroposterior image of the patient's lungs is obtained by the CBCT machine 50 and in step 706, the CBCT machine 50 is centered and an angle of the CBCT machine 50 relative to the bed 60 is identified using the (2D) grid structure of sphere markers 220. In step 708, the patient's lungs are imaged using the CBCT machine 50. In step 710, the location of the endoscope or catheter 100 and the area of interest is marked or otherwise identified in the intra-procedure images captured by the CBCT machine 50 using the user interface 26. In step 712, the pre-procedure images and the intra-procedure images are registered with one another, and in step 714, the endoscope or catheter 100 is navigated to the area of interest. In step 716, it is determined if a further intra-procedural scan using the CBCT machine 50 is needed, and if so, the patient's anatomy is imaged a second time using the CBCT machine 50 to confirm the location of the endoscope or catheter 100 relative to the area of interest in step 718. With the location of the endoscope or catheter 100 relative to the area of interest confirmed, the area of interest is treated in step 720. If no further scan is required, step 718 is skipped and the area of interest is treated in step 720.

Figure 10:
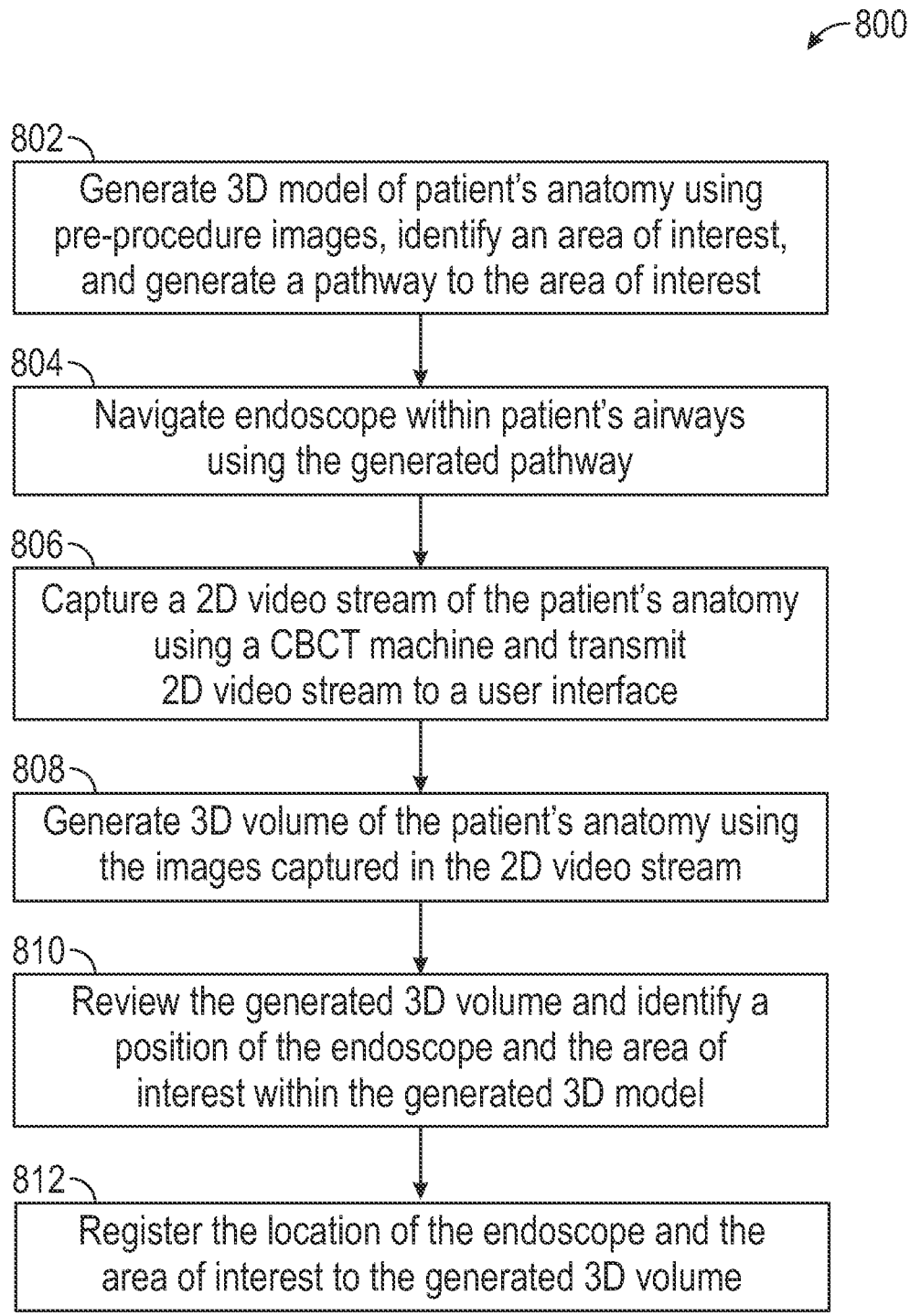
FIG. 10 is a flow diagram illustrating yet another method of performing a surgical procedure in accordance with aspects of the present disclosure.

Referring to FIG. 10, another embodiment of a method of navigating a surgical instrument to an area of interest is illustrated and generally identified by reference numeral 800. In step 802, a 3D model is generated from pre-procedure images and an area of interest, and a pathway thereto, is identified in the 3D model. In step 804, the endoscope or catheter 100 is navigated within the patient's airways using the plan generated in step 802. In step 806, a 2D video stream is captured by the CBCT machine 50 and transmitted to the user interface 26 for review by the user. Using the 2D video stream, in step 808, a 3D volume of the patient's anatomy is generated and the location of the endoscope or catheter 100 and the area of interest is marked or otherwise indicated in the 3D volume using the user interface 26 in step 810. In step 812, the location of the endoscope or catheter 100 and the area of interest is locally registered to the 3D volume.

Figure 11:
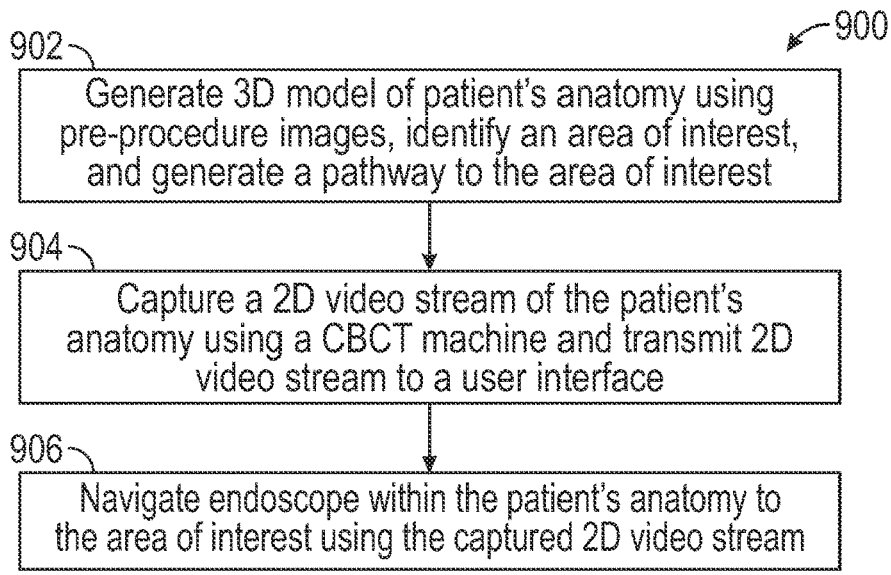
FIG. 11 is a flow diagram illustrating another method of performing a surgical procedure in accordance with aspects of the present disclosure.

With reference to FIG. 11, yet another embodiment of a method of navigating a surgical instrument to an area of interest is illustrated and generally identified by reference numeral 900. In step 902, a 3D model of the patient's lungs is generated from pre-procedure CT images and an area of interest, and a pathway thereto, is identified in the 3D model. In step 904, a 2D video stream is captured by the CBCT machine 50 and transmitted to the user interface 26 for review by the user. In step 906, the endoscope or catheter 100 is navigated to the area of interest within the patient's airways utilizing the 3D model of the patient's lungs and the 2D video stream captured by the CBCT machine 50.

Figure 12:
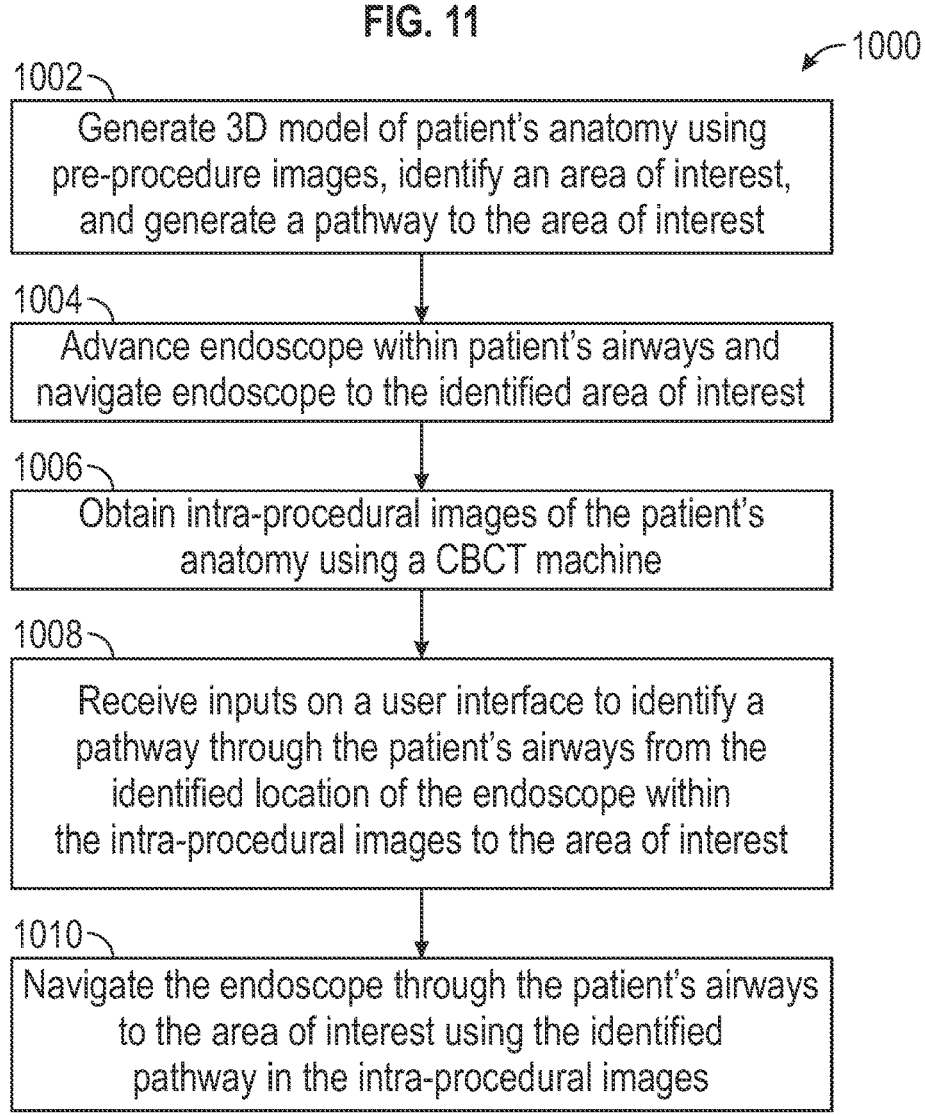
FIG. 12 is a flow diagram illustrating still another method of performing a surgical procedure in accordance with aspects of the present disclosure.

Turning to FIG. 12, another embodiment of a method of navigating a surgical instrument to an area of interest is illustrated and generally identified by reference numeral 1000. In step 1002, a 3D model of the patient's lungs is generated from pre-procedure CT images and an area of interest, and a pathway thereto, is identified in the 3D model. In step 1004, the endoscope or catheter 100 is navigated within the patient's lungs using the 3D model of the patient's lungs. In step 1006, the patient is scanned using the CBCT machine 50 and the intra-procedure images captured by the CBCT machine 50 are displayed on the user interface 26 in step 1008. In step 1008, using the user interface 26, inputs on the user interface are utilized to identify a pathway through the patient's luminal network from the identified location of the endoscope or catheter 100 within the intra-procedure images to the area of interest. In step 1010, the endoscope or catheter 100 is navigated to the area of interface using the pathway identified in the intra-procedure images on the user interface 26.

Although described generally hereinabove, it is envisioned that the memory 32 may include any non-transitory computer-readable storage media for storing data and/or software including instructions that are executable by the processor 30 and which control the operation of the controller 20 and, in some embodiments, may also control the operation of the endoscope or catheter 100. In an embodiment, memory 32 may include one or more storage devices such as solid-state storage devices, e.g., flash memory chips. Alternatively, or in addition to the one or more solid-state storage devices, the memory 32 may include one or more mass storage devices connected to the processor 30 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 30. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the controller 20.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of performing a surgical procedure, comprising:
   obtaining images of a patient's anatomy using a cone beam computed tomography machine while the patient is sedated;
   identifying an area of interest in the images obtained by the cone beam computed tomography machine;
   identifying a pathway to the identified area of interest using the images obtained by the cone beam computed tomography machine; and
   navigating a catheter within the patient's airways to the identified area of interest using the identified pathway.

2. The method according to claim 1, wherein obtaining the images of the patient's anatomy includes obtaining the images of a patient's anatomy using a fixed cone beam computed tomography machine while the patient is sedated.

3. The method according to claim 1, wherein obtaining the images of the patient's anatomy includes obtaining the images of a patient's anatomy using a mobile cone beam computed tomography machine while the patient is sedated.

4. The method according to claim 1, further comprising generating a three-dimensional model of the patient's anatomy from the images obtained by the cone beam computed tomography machine.

5. The method according to claim 4, wherein identifying the area of interest includes identifying the area of interest within the three-dimensional model of the patient's anatomy.

6. The method according to claim 1, further comprising registering a location of the catheter within the patient's anatomy to the images obtained by the cone beam computed tomography machine.

7. The method according to claim 1, wherein obtaining images of the patient's anatomy includes obtaining images of the patient's anatomy using the cone beam computed tomography machine while the patient is sedated and before advancement of the catheter within the patient's body cavity.

8. A method of performing a surgical procedure, comprising:
   navigating a catheter to a lobe of a patient's lung including an area of interest;
   obtaining images of the patient's anatomy using a cone beam computed tomography machine;
   identifying the area of interest in the images obtained by the cone beam computed tomography machine;
   identifying a pathway to the area of interest using the images obtained by the cone beam computed tomography machine; and
   navigating the catheter to the area of interest using the identified pathway.

9. The method according to claim 8, wherein obtaining the images of the patient's anatomy includes obtaining the images of a patient's anatomy using a fixed cone beam computed tomography machine.

10. The method according to claim 8, wherein obtaining the images of the patient's anatomy includes obtaining the images of a patient's anatomy using a mobile cone beam computed tomography machine.

11. The method according to claim 8, further comprising generating a three-dimensional model of the patient's anatomy from the images obtained by the cone beam computed tomography machine.

12. The method according to claim 11, wherein identifying the area of interest includes identifying the area of interest within the three-dimensional model of the patient's anatomy.

13. The method according to claim 8, further comprising registering a location of the catheter within the patient's anatomy to the images obtained by the cone beam computed tomography machine.

14. The method according to claim 8, further comprising obtaining an anteroposterior image of the patient's anatomy using the cone beam computed tomography machine and identifying an angle of the cone beam computed tomography machine when the anteroposterior image was obtained.

15. The method according to claim 14, further comprising identifying a location of a portion of the catheter within the images obtained by the cone beam computed tomography machine.

16. The method according to claim 15, further comprising registering the identified location of the catheter to the images obtained by the cone beam computed tomography machine.

17. A system for performing a surgical procedure, comprising:
   a cone beam computed tomography machine;
   a catheter configured to be navigated within a patient's airways; and
   a controller operably coupled to the cone beam computed tomography machine, the controller including a memory and a processor, the memory storing instructions, which when executed by the processor cause the processor to:
      obtain images of a patient's anatomy using the cone beam computed tomography machine while the patient is sedated;
      identify an area of interest in the images obtained by the cone beam computed tomography machine;
      identify a pathway to the identified area of interest using the images obtained by the cone beam computed tomography machine; and aid navigation of the catheter within the patient's airways to the identified area of interest using the identified pathway.

18. The system according to claim 17, wherein the cone beam computed tomography machine is a fixed cone beam computed tomography machine.

19. The system according to claim 17, wherein the cone beam computed tomography machine is a mobile cone beam computed tomography machine.

20. The system according to claim 17, wherein the instructions, when executed by the processor, cause the processor to obtain images of the patient's anatomy using the cone beam computed tomography machine while the patient is sedated and before advancement of the catheter within the patient's body cavity.

* * * * *